(12) United States Patent
Schlienger et al.

(10) Patent No.: US 8,262,658 B2
(45) Date of Patent: Sep. 11, 2012

(54) INTRAMEDULLARY NAIL

(75) Inventors: Andre Schlienger, Basel (CH); Markus Buettler, Oensingen (CH); Robert Frigg, Bettlach (CH)

(73) Assignee: Synthes USA, LLC, West Chester, PA (US)

(*) Notice: Subject to any disclaimer, the term of this patent is extended or adjusted under 35 U.S.C. 154(b) by 731 days.

(21) Appl. No.: 11/823,766

(22) Filed: Jun. 27, 2007

(65) Prior Publication Data

US 2008/0009869 A1  Jan. 10, 2008

Related U.S. Application Data

(63) Continuation of application No. PCT/CH2004/000758, filed on Dec. 31, 2004.

(51) Int. Cl.
*A61B 17/72* (2006.01)
(52) U.S. Cl. .......................................................... 606/64
(58) Field of Classification Search ............... 606/62–68
See application file for complete search history.

(56) References Cited

U.S. PATENT DOCUMENTS

| | | | | |
|---|---|---|---|---|
| 2,998,007 A | * | 8/1961 | Herzog | 606/63 |
| 3,709,218 A | * | 1/1973 | Halloran | 606/64 |
| 3,846,846 A | * | 11/1974 | Fischer | 623/23.18 |
| 4,055,172 A | * | 10/1977 | Ender et al. | 606/62 |
| 4,135,507 A | * | 1/1979 | Harris | 606/62 |
| 4,169,470 A | * | 10/1979 | Ender et al. | 606/62 |
| 4,475,545 A | * | 10/1984 | Ender | 606/64 |
| 4,919,673 A | * | 4/1990 | Willert et al. | 623/23.48 |
| 5,041,115 A | * | 8/1991 | Frigg et al. | 606/62 |
| 5,066,296 A | * | 11/1991 | Chapman et al. | 606/64 |
| 5,536,269 A | * | 7/1996 | Spievack | 606/63 |
| 5,569,249 A | * | 10/1996 | James et al. | 606/62 |
| 5,697,930 A | * | 12/1997 | Itoman et al. | 606/62 |
| 6,010,506 A | * | 1/2000 | Gosney et al. | 606/62 |
| 6,120,504 A | * | 9/2000 | Brumback et al. | 606/62 |

(Continued)

FOREIGN PATENT DOCUMENTS

CH    647 613 A5    6/1990

(Continued)

OTHER PUBLICATIONS

Definition of curved. Merriam-Webster Dictionary, retrieved Jul. 28, 2009.*

*Primary Examiner* — Eduardo C Robert
*Assistant Examiner* — Jerry Cumberledge
(74) *Attorney, Agent, or Firm* — Fay Kaplun & Marcin, LLP

(57) ABSTRACT

An intramedullary nail, particular for use with a tibia, may have a proximal end part, a distal end part adapted to be introduced into a medullary space, and a central section. The central section includes a first curved section having a first length with a first radius of curvature, and a second curved section having a second length shorter than the first length and a second radius of curvature smaller than the first radius of curvature. The second radius of curvature may be less than the first radius of curvature. The intramedullary nail also includes a central axis. Tangents at two end points of the central section, including the first and second curved sections, enclose an angle gamma between about 9° and about 12°. The intramedullary nail may have a total length ranging from 200 to 500 mm.

18 Claims, 1 Drawing Sheet

| U.S. PATENT DOCUMENTS | | | |
|---|---|---|---|
| 6,547,791 B1 * | 4/2003 | Buhren et al. | 606/62 |
| 2002/0099379 A1 * | 7/2002 | Adam | 606/67 |
| 2002/0183750 A1 | 12/2002 | Buhler et al. | |
| 2003/0069581 A1 | 4/2003 | Stinson et al. | |
| 2005/0277936 A1 * | 12/2005 | Siravo et al. | 606/62 |

FOREIGN PATENT DOCUMENTS

| EP | 0 827 717 A | 3/1998 |
|---|---|---|
| TW | 391242 | 5/2000 |
| WO | WO 00/71040 A | 11/2000 |

* cited by examiner

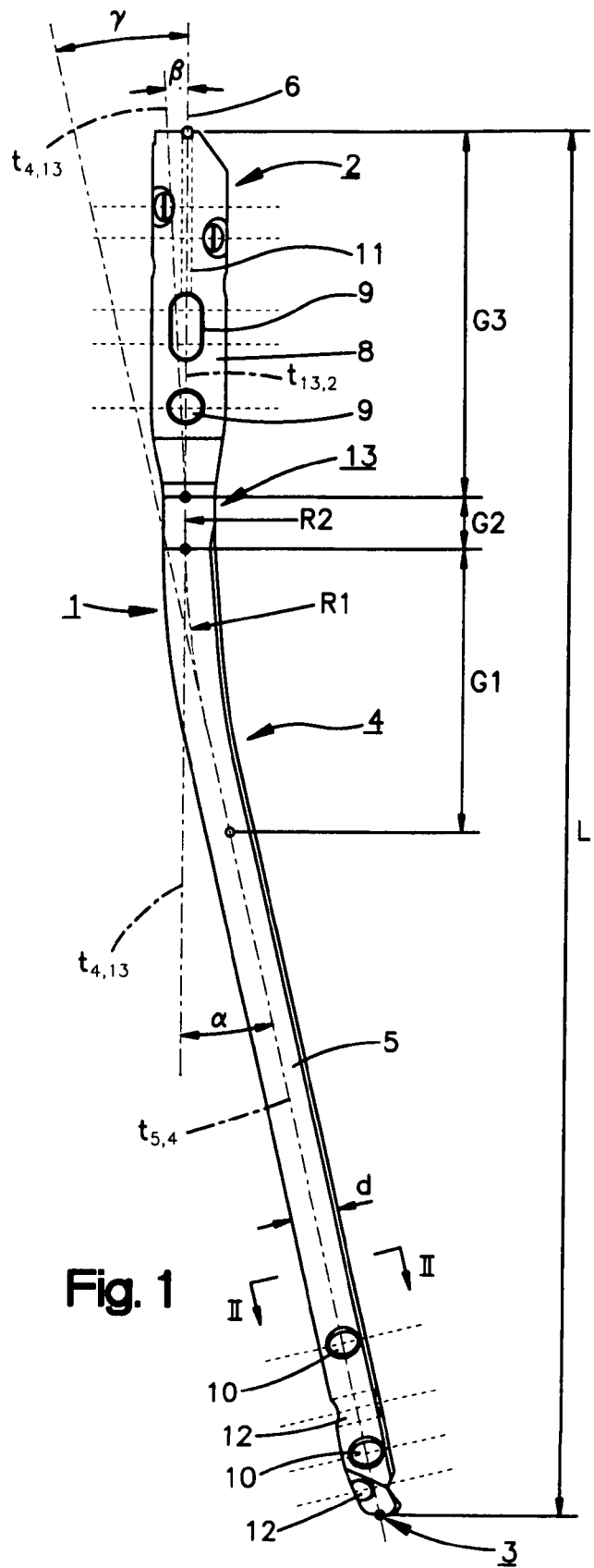
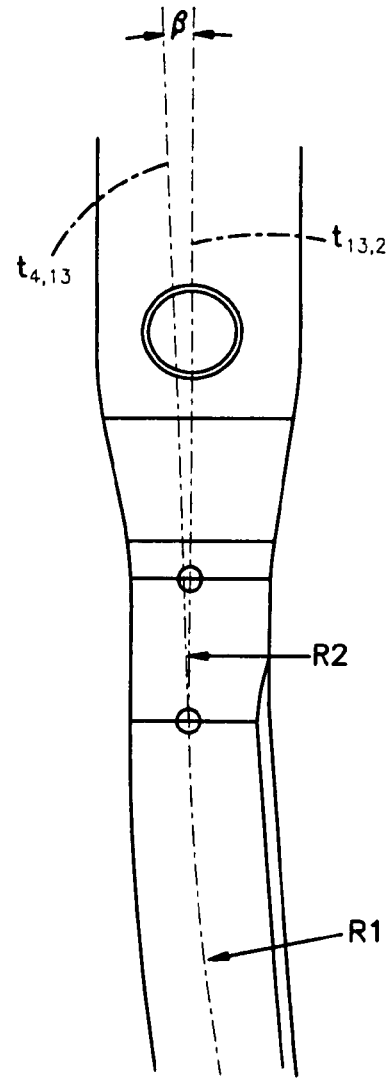
Fig. 3
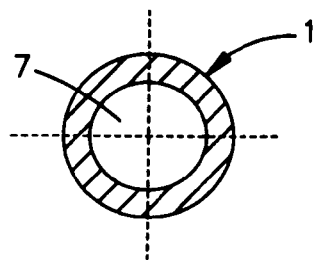
Fig. 2
Fig. 1

INTRAMEDULLARY NAIL

CROSS REFERENCE TO RELATED APPLICATION

This application is a continuation of International Patent Application No. PCT/CH2004/000758, filed Dec. 31, 2004, the entire contents of which is expressly incorporated herein by reference.

TECHNICAL FIELD

The invention relates to an intramedullary nail, particularly for use in the tibia.

BACKGROUND OF THE INVENTION

U.S. Pat. No. 6,010,506 to GOSNEY describes a generic intramedullary nail. The intramedullary nail has a proximal end part which can be pressed on, and a distal end part. The proximal end and the distal end are at an angle relative to one another by means of several curved segments which are disposed between the end parts. In addition, the proximal end part is bent at right angles so that a relatively large angle is formed between the tangents to the central axes at the axial ends. A disadvantage of this known intramedullary nail that it is not suitable for use in relatively linear, tubular bones, especially the tibia.

SUMMARY OF THE INVENTION

The present invention is to provide a remedy for the above-discussed disadvantage. It is an object of the invention to produce an intramedullary nail having a central section comprising of several curved sections. The tangents at the two end points of this central section encloses a relatively small angle. That is, an angle which is suitable particularly for linear, tubular bones.

Pursuant to the invention, this objective is accomplished with an intramedullary nail having a proximal end part, a distal end part, and a central section. The central section includes a first curved section having a first length with a first radius of curvature, and a second curved section having a second length shorter than the first length and a second radius of curvature smaller than the first radius of curvature. The intramedullary nail also includes a central axis. Tangents at two end points of the central section, including the first and second curved sections, enclose an angle gamma between about 9° and about 12°. The intramedullary nail may have a total length ranging from 200 to 500 mm.

Some advantages achieved by the intramedullary nail of this application are that:

the intramedullary nail having a central section comprising of two curved sections, because of the two curvatures, which have a different radius, the intramedullary nail can be adapted optimally to a medullary canal;

the tangents at the end points of the central section enclose an angle gamma of between 9° and 12° such that the intramedullary nail is suitable for relatively linear tubular bones, especially for the tibia, and because of the small angle gamma, it is possible to insert the intramedullary nail into a medullary space without using much force.

In different embodiments, the intramedullary nail may have the following distinguishing features:

the length of the proximal end part $G_3$ ranges from ⅙ L to ⅓ L, where L is the total length of the intramedullary nail;

the tangents at the two end points of the first curved section enclose an angle alpha ranging from about 7° to about 10°, and preferably from about 8° to about 9°;

the tangents at the two end points of the second curved section enclose an angle beta ranging from about 1° to about 3°;

the first curved end section of length $G_1$ has a radius of curvature $R_1$ ranging from about 300 to about 1,300 mm;

the ratio of the total length of the intramedullary nail to the radius of the curvature of the first curved section ($L/R_1$) ranges from about 0.2 to about 0.8;

the length (l) of the straight, distal part ranges from about 0.20 L to about 0.55 L, and preferably from about 0.25 to about 0.50 L;

the length $G_1$ of the first curved section ranges from about 0.2 L to about 0.4 L; and the radius of curvature $R_2$ of the second curved section ranges from about 10 mm to about 50 mm.

In a further embodiment, the proximal end part axially adjoins the second curved section and is formed as a straight proximal section.

In still a different embodiment, the distal end part is constructed as a straight section.

Due to the formation of one or both end parts as straight sections, an advantage can be attained that the curvature of the intramedullary nail is slight. As a result, the intramedullary nail is particularly suitable for straight, tubular bones.

In a further embodiment, the intramedullary nail may have a longitudinal borehole which is coaxial with the central axis.

In yet another embodiment, there may be at least one locking hole which extends transversely to the central axis and is suitable for accommodating a screw, in the region of the proximal end part.

In a further embodiment, there may be at least one locking hole, extending transversely to the central axis and is also suitable for accommodating a screw, in the region of the distal end part.

In yet a further embodiment, there may be two locking holes, extending transversely to the central axis and enclose with one another an angle preferably of about 45° to about 90°, in the region of the distal end part.

In another embodiment, the distal end part may have four locking holes. The distance of the proximally located central locking hole to the other two locking holes may be different.

An implantation method of a cannulated intramedullary nail may include the following steps:

Step A: Bringing about and maintaining the optimum setting, depending on the type of fracture;

Step B: Opening the medullary canal with the help of an opening instrument so that the entry angle and the orientation with respect to the medullary canal are correct, depending on the surgical technique used;

Step C: Introducing a guide wire up into the distal, future end position of the intramedullary nail and determining the length of the intramedullary nail required;

Step D: The intramedullary nail, pre-mounted on the insertion handle, is brought by means of the guide wire through the opening channel into the medullary space;

Step E: After the axial position of the intramedullary nail is checked and repositioned, the intramedullary nail is locked into place by one of various locking options.

BRIEF DESCRIPTION OF THE DRAWINGS

The intramedullary nail is explained in even greater detail in the following exemplary drawings. The intramedullary nail may be better understood by reference to the following drawings, wherein like references numerals represent like elements. The drawings are merely exemplary to illustrate the structure, operation and method of use of the intramedullary nail and certain features that may be used singularly or in combination with other features and the invention should not be limited to the embodiments shown.

FIG. 1 shows a longitudinal section through an embodiment of the inventive intramedullary nail, FIG. 2 shows a section along the line II-II of FIG. 1, and FIG. 3 shows an enlarged section in the region of the second, curved section of the embodiment of the inventive intramedullary nail shown in FIGS. 1 and 2.

DESCRIPTION OF THE PREFERRED EMBODIMENTS

The intramedullary nail 1, shown in FIGS. 1 to 3, may comprise a central axis 6, a proximal end part 2, a distal end part 3 that is suitable for introduction into the intramedullary space and two curved sections 4; 13 disposed axially one behind the other. The total length of the intramedullary nail "L" ranges from about 200 mm to about 500 mm. Axially, the proximal end part 2 adjoins the second, curved section 13 and is constructed as a straight, proximal section 8 of length $G_3$. Length $G_3$ may be less than or equal to the total length L of the intramedullary nail and preferably ranges between about ⅙L to about ⅓L. The distal end part 3 may be constructed as a straight, distal section 5 with a length "l" ranging from about 0.20L to about 0.55L, and preferably from about 0.25L to about 0.50L. The first curved section 4 may have a length $G_1$ that is less than or equal to L, and preferably ranges from about 0.2L to about 0.4L. The first curved section may have a radius of curvature $R_1$ ranging from about 300 mm to about 1,300 mm, where a ratio between the total length of the intramedullary nail and the radius of the curvature ($L/R_1$) is between about 0.2 to about 0.8. The second curved section 13, disposed between the proximal end part 2 and the first curved section 4, may have a length $G_2$ which may be less than or equal to length $G_1$, and a radius curvature $R_2$ which may be less than $R_1$. Preferably the radius of curvature $R_2$ ranges from about 10 mm to about 50 mm. Tangents $t_{5,4}$ and $t_{13,2}$ at the two end points of a middle section, enveloping the two curved sections 4; 13, enclose an angle gamma of about 9° to about 12°, and preferably about 10° and coincide proximally with the central axis 6 of the straight, proximal section 8 and distally with the central axis 6 of the straight, distal section 5. Furthermore, the tangents $t_{5,4}$ and $t_{4,13}$ at the two end points of the first curved section 4 enclose an angle alpha of about 7° to about 10°, and preferably from about 8° to about 9°. The tangents $t_{4,13}$ and $t_{13,2}$ at the two end points of the second curved section 13 enclose an angle beta of about 1° to about 3°, and preferably about 2°.

Both curvatures of the intramedullary nail lie in the plane of the drawing, which, after the implantation of the intramedullary nail 1, corresponds to the anatomical medio-lateral plane. That is, the intramedullary nail, when implanted, is bent in the antero-posterior direction.

The intramedullary nail may have a continuous longitudinal borehole 7 which is coaxial with the central axis 6 (see FIG. 2).

In the region of the proximal end part 2 of the intramedullary nail 1, there may be one to four locking holes 9 which extend transversely to the central axis 6. One of the four locking holes 9 may be constructed as an elongated hole, in order to be able to carry out a compression. So as to lock or secure of the intramedullary nail 1, screws (not shown) may be inserted into the locking holes 9 in the region of the proximal end part 2.

In the region of the distal end part 3, there may be one to four locking holes 10, 12 which extend transversely to the central axis 6. These locking holes 10, 12 may be disposed in different radial directions and enclose different angles with one another. Moreover, the distances between the central locking hole 12 and the other two locking holes 10 may be different. In one embodiment, there may be two locking holes, which extend transversely to the central axis and enclose with one another an angle preferably of about 45° to 90°. In another embodiment, the distal end part 3 may have three locking holes, where the distance between the central locking hole and the other two locking holes is different.

A cannulated, intramedullary nail may be implanted in the method described below. The method includes the steps of first bringing about and maintaining the optimum setting which depends on the type of fracture. Next, opening the medullary canal of the of the bone in which the intramedullary nail is to be inserted with the help of an opening instrument, so that the entry angle and the orientation with respect to the medullary canal are correct. The entry angle and orientation may depend on the surgical technique used. A guide wire is introduced into the distal, future end position of the intramedullary nail. In this step, determination of the length of the intramedullary nail required. The intramedullary nail, pre-mounted on an insertion handle is brought by means of the guide wire through the opening channel into the medullary space. After the axial position of the intramedullary nail is checked and repositioned, the intramedullary nail is locked/secured in place by various locking options, for example screws inserted through the locking holes described above.

It is contemplated that the features of the above embodiments of the intramedullary nail may be combined in a number of combinations to produce derivative embodiments. Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. An intramedullary nail comprising:
a proximal end part;
a straight distal end part extending proximally from a distal end of the nail;
a central section extending proximally from a proximal end of the distal end part to a distal end of the proximal end part, wherein the central section includes a first curved section having a first length with a first radius of curvature, and a second curved section having a second length shorter than the first length and a second, non-zero radius of curvature smaller than the first radius of curvature; and a central axis, wherein tangents at two end points of the central section, including the first and second curved sections enclose an angle gamma between about 9° and about 12°, and wherein the intramedullary nail has a total length ranging from 200 to 500 mm.

2. An intramedullary nail according to claim 1, wherein the proximal end part has a length ranging from 1/6 to 1/3 of the total length of the intramedullary nail.

3. An intramedullary nail according to claim 1, wherein tangents at two end points of the first curved section enclose an angle alpha ranging from about 7° to about 10°.

4. An intramedullary nail according to claim 3, wherein the angle alpha ranges from about 8° to about 9°.

5. An intramedullary nail according to claim 1, wherein tangents at two end points of the second curved section enclose an angle beta ranging from about 1° to about 3°.

6. An intramedullary nail according to claim 1, wherein the proximal end part axially adjoins the second curved section and is constructed as a straight section.

7. An intramedullary nail according to claim 1, wherein the first curved section has a radius of curvature ranging from about 300 to about 1300 mm.

8. An intramedullary nail according to claim 1, wherein a ratio of the total length of the intramedullary nail to the radius of the first curved section ranges from about 0.2 to about 0.8.

9. An intramedullary nail according to claim 1, wherein the distal end part has a length between about 0.20 to about 0.55 of the total length of the intramedullary nail.

10. An intramedullary nail according to claim 1, wherein the distal end part has a length about 0.25 of the total length of the intramedullary nail.

11. An intramedullary nail according to claim 1, wherein the intramedullary nail has a longitudinal borehole which is coaxial with the central axis.

12. An intramedullary nail according to claim 1, wherein the proximal end part has at least one locking hole extending transversely to the central axis.

13. An intramedullary nail according to claim 1, wherein the distal end part has at least one locking hole extending transversely to the central axis.

14. An intramedullary nail according to claim 1, wherein the distal end part has at least two locking holes extending transversely to the central axis.

15. An intramedullary nail according to claim 14, wherein the two locking holes extend transversely to the central axis and enclose an angle of about 45° to about 90° with one another.

16. An intramedullary nail according to claim 1, wherein the distal end part has three locking holes, wherein a distance between a central locking hole and the other two locking holes is different.

17. An intramedullary nail according to claim 1, wherein the first curved section has a length ranging from about 0.2 to about 0.4 of the total length of the intramedullary nail.

18. An intramedullary nail according to claim 1, wherein the second curved section has a radius ranging from about 10 to about 50 mm.

* * * * *